(12) United States Patent
Duff et al.

(10) Patent No.: US 7,473,785 B2
(45) Date of Patent: Jan. 6, 2009

(54) PHOTOCONDUCTIVE MEMBERS

(75) Inventors: James McConnell Duff, Mississauga (CA); Timothy P. Bender, Toronto (CA); Cuong Vong, Hamilton (CA); John F. Graham, Oakville (CA)

(73) Assignee: Xerox Corporation, Norwalk, CT (US)

( * ) Notice: Subject to any disclaimer, the term of this patent is extended or adjusted under 35 U.S.C. 154(b) by 299 days.

(21) Appl. No.: 11/299,500

(22) Filed: Dec. 12, 2005

(65) Prior Publication Data

US 2007/0135646 A1     Jun. 14, 2007

(51) Int. Cl.
C07D 235/02 (2006.01)
C07D 235/12 (2006.01)

(52) U.S. Cl. .................. 548/301.7; 548/304.4

(58) Field of Classification Search .............. 548/301.7, 548/312.7, 314.4, 304.4
See application file for complete search history.

(56) References Cited

U.S. PATENT DOCUMENTS

| | | | |
|---|---|---|---|
| 3,121,006 A | 2/1964 | Middleton et al. | 430/31 |
| 4,265,990 A | 5/1981 | Stolka et al. | 430/58.8 |
| 4,298,697 A | 11/1981 | Baczek et al. | 521/27 |
| 4,338,380 A | 7/1982 | Erickson et al. | 428/594 |
| 4,419,427 A | 12/1983 | Graser et al. | 430/58.6 |
| 4,429,029 A | 1/1984 | Hoffmann et al. | 430/58.6 |
| 4,464,450 A | 8/1984 | Teuscher | 430/58.8 |
| 4,501,906 A | 2/1985 | Spietschka et al. | 549/232 |
| 4,555,463 A | 11/1985 | Hor et al. | 430/57.3 |
| 4,560,635 A | 12/1985 | Hoffend et al. | 430/108.2 |
| 4,587,189 A | 5/1986 | Hor et al. | 430/58.8 |
| 4,709,029 A | 11/1987 | Spietschka et al. | 544/125 |
| 4,714,666 A | 12/1987 | Wiedemann et al. | 430/59.1 |
| 4,921,773 A | 5/1990 | Melnyk et al. | 430/132 |
| 4,937,164 A | 6/1990 | Duff et al. | 430/58.8 |
| 4,968,571 A | 11/1990 | Gruenbaum et al. | 430/59.1 |
| 5,019,473 A | 5/1991 | Nguyen et al. | 430/59.1 |
| 5,225,307 A | 7/1993 | Hor et al. | 430/136 |
| 5,336,577 A | 8/1994 | Spiewak et al. | 430/58.25 |
| 5,473,064 A | 12/1995 | Mayo et al. | 540/141 |
| 5,645,965 A | 7/1997 | Duff et al. | 430/58.8 |
| 5,756,245 A | 5/1998 | Esteghamatian et al. | 430/58.8 |
| 5,856,508 A * | 1/1999 | Jaffe et al. | 548/301.7 |
| 6,051,351 A | 4/2000 | Hsiao et al. | 430/59.1 |
| 6,194,110 B1 | 2/2001 | Hsiao et al. | 430/58.7 |
| 6,319,645 B1 | 11/2001 | Murti et al. | 430/58.65 |
| 6,322,941 B1 | 11/2001 | Hsiao et al. | 430/58.65 |
| 6,562,981 B2 * | 5/2003 | Otani et al. | 548/301.7 |
| 6,656,651 B1 | 12/2003 | Bender et al. | 430/58.8 |
| 6,756,169 B2 | 6/2004 | Lin et al. | 430/78 |

FOREIGN PATENT DOCUMENTS

| | | |
|---|---|---|
| EP | 0 320 201 | 6/1989 |
| EP | 0 349 219 | 1/1990 |
| JP | 45020981 B4 * | 7/1970 |

OTHER PUBLICATIONS

Otani et al., Time-resolved study of intramolecular charge transfer fluorescence in 1,2,3,4-tetrachloro-11H-isoindolo-[2,1-a]-benzimidazol-11-one,2003, Journal of Luminescence, vol. 104, 273-274.*
Alkhathlan et al., Spectroscopic Studies of Benzimidazole, Quinoxaline and Quinoline Derviatives, 1995, J. Chem. Research (S), 10.*
Niyazi et al., The Chemical Polyfunctional Additives for the Heterochain Polymers, 1994, Polym. Yearb., vol. 11, 164.*
U.S. Patent Application filed Dec. 12, 2005, of James McConnell Duff et al., entitled "Photoconductive Members" 28 pages, not yet published.
U.S. Patent Application filed Dec. 12, 2005, of James McConnell Duff et al., entitled "Photoconductive Members" 45 pages, not yet published.
U.S. Patent Application filed Dec. 12, 2005, of James McConnell Duff et al., entitled "Photoconductive Members" 42 pages, not yet published.
Supplemental Information Disclosure Statement filed Apr. 18, 2007 in copending application of James McConnell Duff et al., U.S. Appl. No. 11/299,498, 3 pages.
European Search Report issued for European Patent Application No. 06124556.9—1217 (corresponding to U.S. Appl. No. 11/299,498), dated Mar. 21, 2007, 6 pages.
Response to Official Communication issued in European Patent Application No. 06124556.9-1217 (corresponding to U.S. Appl. No. 11/299,498) filed May 13, 2008, 8 pages.
Office Action mailed May 9, 2008 in copending application of Jame McConnell Duff et al., U.S. Appl. No. 11/299,498, 7 pages.

* cited by examiner

Primary Examiner—Kamal A Saeed
Assistant Examiner—Kristin Bianchi
(74) Attorney, Agent, or Firm—Marylou J. Lavoie, Esq. LLC

(57) ABSTRACT

A compound comprising a tetrahalobenzamidazolebenzene or a bis(tetrahalophenyl)biphenylbisimidazole of the alternative following formulas or dimers thereof

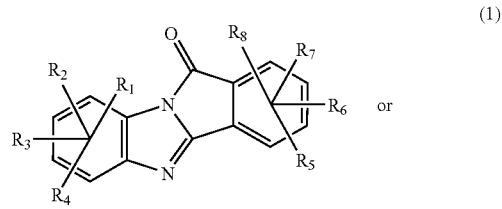

(1)

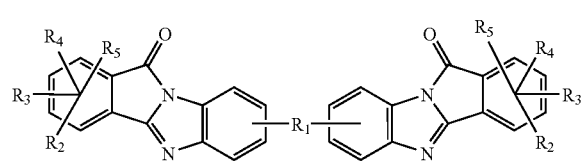

(2)

wherein each of $R_1$, $R_2$, $R_3$, $R_4$, and $R_5$ are the same or different and are independently selected from the group comprising hydrogen, alkyl, aryl, and halogen.

16 Claims, No Drawings

PHOTOCONDUCTIVE MEMBERS

RELATED APPLICATIONS

Commonly assigned, co-pending U.S. patent application of James McConnell Duff, Timothy P. Bender, Cuong Vong, and John F. Graham, Ser. No. 11/301,233, entitled "Photoconductive Members," filed of even date herewith, which is hereby incorporated by reference herein in its entirety, describes imaging members and more specifically layered photoconductive imaging members comprising for example bisbenzamidazoleperinones.

Commonly assigned, co-pending U.S. patent application of James McConnell Duff, Timothy P. Bender, Cuong Vong, and John F. Graham, Ser. No. 11/301,217, entitled "Photoconductive Members,"filed of even date herewith, which is hereby incorporated by reference herein in its entirety, describes imaging members and more specifically bisbenzamidazoleperinone compounds.

Commonly assigned, co-pending U.S. patent application of James McConnell Duff, Timothy P. Bender, Cuong Vong, and John F. Graham, Ser. No. 11/299,498, entitled "Photoconductive Members," filed of even date herewith, which is hereby incorporated by reference herein in its entirety, describes imaging members and more specifically imaging members comprising tetrahalobenzamidazolebenzene and bis(tetrahalophenyl)biphenylbisimidazole compounds.

BACKGROUND

The present disclosure is generally related to imaging members and more specifically related to layered photoconductive imaging members comprising for example bis(tetrahalophenyl)biphenylbisimidazole dimers or tetrahalobenzamidazolebenzene dimers. Photoconductive imaging members containing the aforementioned components possess in embodiments a number of advantages as indicated herein, inclusive of being sensitive to blue wavelengths of, for example, about 900 to about 300 nanometers, and in particular, from about 350 to about 450 nanometers or about 370 to about 425 nanometers. The photogenerating layer, which can be exposed to light of the appropriate blue wavelengths simultaneously, or sequentially, exhibits, for example, excellent cyclic stability, independent layer discharge, acceptable dark decay characteristics, permits tuning of the electrical properties of the imaging member, and enables substantially no adverse changes in performance over extended time periods. Processes of imaging, especially imaging and printing, including digital, are also encompassed by the present disclosure.

The layered photoconductive imaging members illustrated herein can be selected for a number of different known imaging and printing processes including, for example, multicopy/fax devices, electrophotographic imaging processes, especially xerographic imaging and printing processes wherein negatively charged or positively charged images are rendered visible with toner compositions of an appropriate charge polarity. The imaging members as indicated herein are in embodiments sensitive in the wavelength region of, for example, from about 900 to about 300 nanometers, and in particular, from about 350 to about 450 nanometers, or from about 370 nanometers to about 425 nanometers. Moreover, the imaging members of the present disclosure in embodiments can be selected for color xerographic imaging applications where several color printings can be achieved in a single pass.

Photoconductive or photoresponsive imaging members are disclosed in the following U.S. Patents, the disclosures of each of which are totally incorporated by reference herein, U.S. Pat. Nos. 4,265,990, 4,419,427, 4,429,029, 4,501,906, 4,555,463, 4,587,189, 4,709,029, 4,714,666, 4,937,164, 4,968,571, 5,019,473, 5,225,307, 5,336,577, 5,473,064, 5,645,965, 5,756,245, 6,051,351, 6,194,110, and 6,656,651. The appropriate components and process aspects of the each of the foregoing U.S. Patents may be selected for the present disclosure in embodiments thereof.

SUMMARY

Imaging members are provided with many of the advantages illustrated herein, including, for example, photoresponsive imaging members with excellent photosensitivity to blue light radiations, layered photoresponsive imaging members with a sensitivity to blue light, and which members possess in embodiments tunable and preselected electricals, acceptable dark decay characteristics, and high photosensitivity. Moreover, provided are improved layered photoresponsive imaging members comprising bis(tetrahalophenyl)biphenylbisimidazole or tetrahalobenzamidazolebenzene dimers with photosensitivity to blue light, for example, in the wavelength region of from about 350 to about 450 nanometers or more specifically 370 to about 425 nanometers. Further provided are photoconductive imaging members with a photogenerating layer comprised of bis(tetrahalophenyl)biphenylbisimidazole or tetrahalobenzamidazolebenzene dimer photogenerating components, and which layer can be deposited on a supporting substrate. The photoresponsive or photoconductive imaging members disclosed can be selected for imaging processes including for example xerography.

Aspects illustrated herein include a photoconductive member component comprising a supporting substrate and thereover a photogenerating layer comprising a tetrahalobenzamidazolebenzene (1) or a bis(tetrahalophenyl)biphenylbisimidazole (2) photogenerating component of the alternative following formulas or dimers thereof

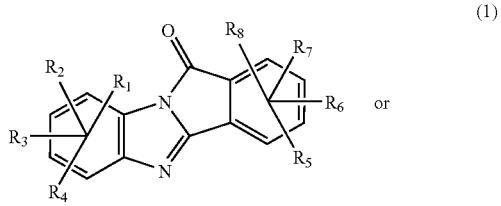

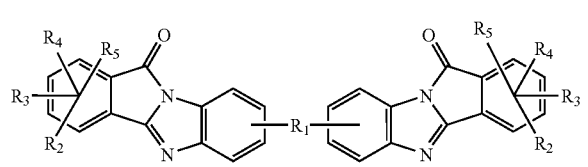

wherein each of $R_1$, $R_2$, $R_3$, $R_4$, $R_5$, $R_6$, $R_7$, and $R_8$ are the same or different and are independently selected from the group consisting of hydrogen, alkyl, aryl, hydrocarbon, which may be optionally substituted or arranged in such a way as to form a cyclic ring, which can be either saturated or unsaturated, and halogen. In embodiments, the alkyl can be selected to contain from about 1 to about 25 carbon atoms. Selected examples of suitable alkyl components can include, but are not limited to, methyl, ethyl, propyl, butyl, pentyl, and higher carbon number straight chained alkyl groups. Optionally the alkyl component can be selected in such a fashion as to form a ring or multi-ringed system. In further embodiments, the aryl can be selected to contain from about 6 to about 48carbon atoms. Selected examples of suitable aryl components include, but are not limited to, phenyl, naphthyl, anthranyl or higher fused aromatic ring systems. In further embodiments, halogen can be selected to include, but is not limited to, fluorine, chlorine, bromine, and iodine. In further embodiments hydrogen can be selected.

Further aspects illustrated herein include a compound having the following formula

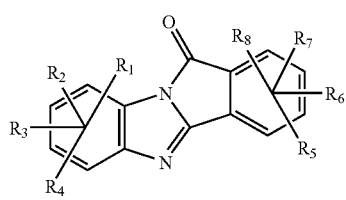

(1)

wherein each of $R_1$, $R_2$, $R_3$, $R_4$, $R_5$, $R_6$, $R_7$, and $R_8$ are the same or different and are independently selected from the group consisting of hydrogen, alkyl, aryl, hydrocarbon, which may be optionally substituted or arranged in such a way as to form a cyclic ring, which can be either saturated or unsaturated, and halogen. In embodiments, the alkyl can be selected to contain from about 1 to about 25 carbon atoms. Selected examples of suitable alkyl components can include, but are not limited to, methyl, ethyl, propyl, butyl, pentyl, and higher straight chained alkyl groups. Optionally the alkyl component may be arranged in such a fashion as to form a ring or multi-ringed system. In further embodiments, the aryl can be selected to contain from about 6 to about 48carbon atoms. Selected examples of suitable aryl components include, but are not limited to, phenyl, naphthyl, anthranyl or higher fused aromatic ring systems. In further embodiments, halogen can be selected to include, but is not limited to, fluorine, chlorine, bromine, and iodine. In further embodiments hydrogen can be selected.

Further aspects illustrated herein include a compound having the following formula

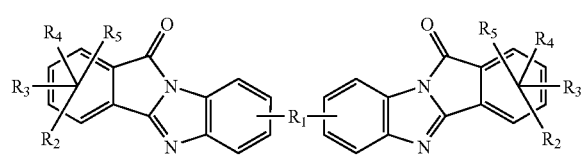

(2)

wherein each of $R_1$, $R_2$, $R_3$, $R_4$, and $R_5$ are the same or different and are independently selected from the group consisting of hydrogen, alkyl, aryl, hydrocarbon, which may be optionally substituted or arranged in such a way as to form a cyclic ring, which can be either saturated or unsaturated, and halogen. In embodiments, the alkyl can be selected to contain from about 1 to about 25 carbon atoms. Selected examples of suitable alkyl components can include, but are not limited to, methyl, ethyl, propyl, butyl, pentyl, and higher straight chained alkyl groups. Optionally the alkyl component may be arranged in such a fashion as to form a ring or multi-ringed system. In further embodiments, the aryl can be selected to contain from about 6 to about 48carbon atoms. Selected examples of suitable aryl components include, but are not limited to, phenyl, naphthyl, anthranyl or higher fused aromatic ring systems. In further embodiments, halogen can be selected to include, but is not limited to, fluorine, chlorine, bromine, and iodine. In further embodiments hydrogen can be selected.

Further aspects illustrated herein include an image forming apparatus for forming images on a recording medium comprising:

a) a photoreceptor member having a charge retentive surface to receive an electrostatic latent image thereon, wherein said photoreceptor member comprises a photoconductive member component comprising a supporting substrate and thereover a photogenerating layer comprising tetrahalobenzamidazolebenzene or a bis(tetrahalophenyl)biphenylbisimidazole photogenerating component of the alternative following formulas or dimers thereof

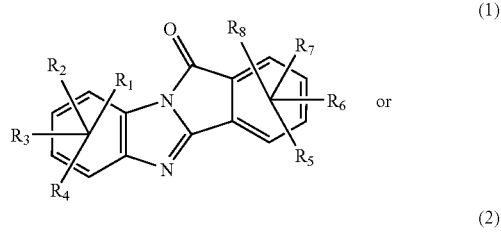

(1) or

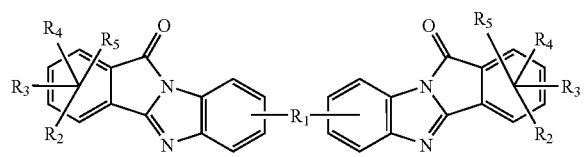

(2)

wherein each of $R_1$, $R_2$, $R_3$, $R_4$, $R_5$, $R_6$, $R_7$, and $R_8$ are the same or different and are independently selected from the group consisting of hydrogen, alkyl, aryl, and halogen;

b) a development component to apply a developer material to said charge-retentive surface to develop said electrostatic latent image to form a developed image on said charge-retentive surface;

c) a transfer component for transferring said developed image from said charge-retentive surface to another member or a copy substrate; and d) a fusing member to fuse said developed image to said copy substrate.

Specific examples of tetrahalobenzamidazolebenzene or bis(tetrahalophenyl)biphenylbisimidazole dimers include those of the following formulas

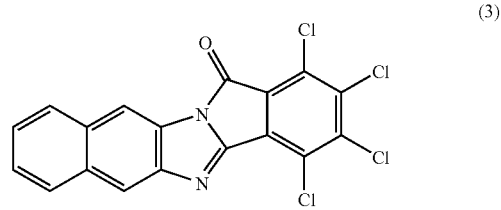

(3)

-continued

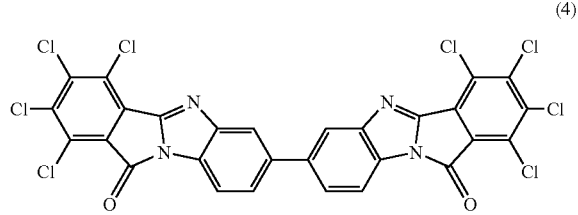

(4)

The tetrahalobenzamidazolebenzene or bis(tetrahalophenyl)biphenylbisimidazole dimers can be prepared by a number of methods such as the reaction of a 3,4,5,6-tetrahalophthalic anhydride with a 1,2-arylene diamine to form a crude product, which may or may not be isolated and/or purified, followed by a process such as crystallization by train sublimation to provide the photogenerator component. Many structural variations of these compounds can be readily prepared and if desired fabricated into a generator layer in a photoreceptive device such as by vacuum evaporation. For example, the following reaction scheme can be selected in embodiments

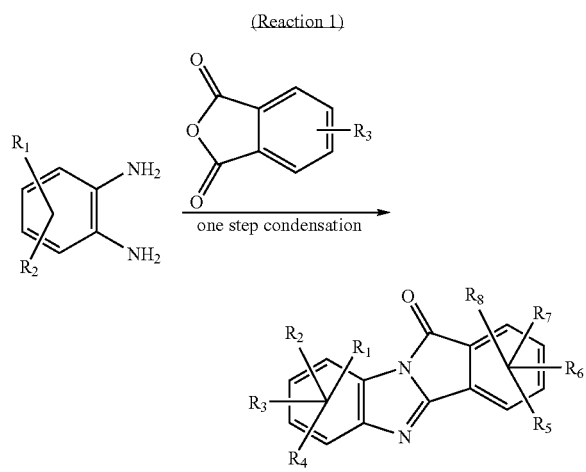

(Reaction 1)

and dimers, wherein each of $R_1$, $R_2$, $R_3$, $R_4$, $R_5$, $R_6$, $R_7$ and $R_8$ are the same or different and are independently selected from the group consisting of hydrogen, alkyl, aryl, and halogen, for example, fluoro/fluoride, chloro/chloride, bromo/bromide or iodo/iodide, and can be selected as described above.

Compounds of this type can be made in general by any suitable process, for example, a one-step one-pot reaction of a tetrahalophthalic anhydride with an equal molar amount or slight molar excess of a 1,2-diaminoarylene compound at temperatures between about 150° C. to about 200° C. in a suitably high boiling polar solvent such as N-methylpyrrolidone, N,N-dimethylacetamide, hexamethylphosphoramine, m-cresol and the like, and usually in the presence of a catalyst selected in an amount of for example between about 1 mol % to about 10 mol %, such as salts of zinc, aluminum, iron, gallium, tin and the like. After a certain period of time at reaction temperature the reaction mixture is cooled and usually diluted with an alcohol such as isopropanol. The crude product which is usually insoluble in alcohol can be isolated by common filtration techniques. A process to purify the compound prior to its utilization as a photogenerator can be selected, such as, for example, fractional or train sublimation.

In embodiments, there is provided a member wherein the photogenerating layer is of a thickness of from about 0.2 to about 20 microns or about 1 to about 5 microns; a member wherein the photogenerator component amount is from about 0.05 weight percent to about 30 weight percent with from about 75 weight percent to about 90 weight percent of binder, and wherein the total of the components is abut 100 percent; and wherein the dimer layer is dispersed in from abut 50 weight percent to about 75 weight percent of a polymer binder; a member wherein that absorbs light of a wavelength of from about 350 to about 450 nanometers or about 370 to about 425 nanometers; an imaging member wherein the supporting substrate is comprised of a conductive substrate comprised of a metal; an imaging member wherein the conductive substrate is aluminum, aluminized polyethylene terephthalate or titanized polyethylene terephthalate; an imaging member wherein the photogenerator binder is selected from the group consisting of polyesters, polyvinyl butyrals, polycarbonates, polystyrene-b-polyvinyl pyridine, and polyvinyl formyls; an imaging member wherein the charge transport layer is a hole transporting layer comprised of arylamine molecules and wherein such a layer is transparent to radiation at between about 350 to about 450 nanometers or about 370 to about 425 nanometers; a method of imaging which comprises generating an electrostatic latent image on the imaging member of the present disclosure, developing the latent image, and transferring the developed electrostatic image to a suitable substrate; a method of imaging wherein the imaging member is exposed to light of a wavelength of from about 350 to about 450 nanometers or about 370 to about 425 nanometers; an imaging apparatus containing a charging component, a development component, a transfer component, and a fixing component and wherein the apparatus contains a photoconductive imaging member comprised of supporting substrate, and thereover a layer comprised of a tetrahalobenzamidazolebenzene or bis(tetrahalophenyl)biphenylbisimidazole photogenerating pigment and a hole transport layer; an imaging apparatus containing a charging component, a development component, a transfer component, and a fixing component, and wherein the apparatus contains a photoconductive imaging member comprised of supporting substrate, and thereover a component as described herein, wherein the component is a photoconductor; an imaging member further containing an adhesive layer and a hole blocking layer; an imaging member wherein the blocking layer is contained as a coating on a substrate and wherein the adhesive layer is coated on the blocking layer; an imaging member further containing an adhesive layer and a hole blocking layer; a method of imaging which comprises generating an electrostatic latent image in the imaging member of the present disclosure, developing the latent image, and transferring the developed electrostatic image to a suitable substrate; and a color method of imaging which comprises generating an electrostatic latent image on the imaging member, developing the latent image, transferring and fixing the developed electrostatic image to a suitable substrate; and photoconductive imaging members with a tetrahalobenzamidazolebenzene or bis(tetrahalophenyl)biphenylbisimidazole photogenerating dimer.

In embodiments, the photogenerating layer can be selected at a thickness of from about 0.2 to about 20 microns, or about 1 to about 5microns, the charge transport layer can be selected at a thickness of from about 10 to about 50 microns, or about 20 to about 30 microns, and each of the layers can be selected to contain from about 10 weight percent to about 75weight percent of a polymer binder, the photogenerating layer can be selected in an amount of from about 5 to about 10 weight percent, and the binder can be selected in an amount of about 50 to about 90 weight percent.

The photogenerating components and the charge transport components are in embodiments dispersed in a suitable binder, for example a polymer binder, such as for example, polycarbonates, polyesters, polyvinylbutyral, polysiloxanes and polyurethanes. The photogenerating pigments can be present in various amounts, such as, for example, from about 0.05 weight percent to about 30 weight percent or from about 0.05 weight percent to about 5 weight percent and the polymer binder can be present in an amount of from about 25 to about 90 weight percent, about 25 weight percent to about 75 weight percent, or about 50 to about 90 weight percent. The thickness of this layer can be, for example, from about 5 microns to about 60 microns or from about 1 micron to about 10 microns.

There can also be selected for members of the present disclosure a suitable adhesive layer, which can be for example situated between the substrate and the single layer, examples of adhesives being polyesters, such as VITEL® PE 100 and PE 200 available from Goodyear Chemicals or MOR-ESTER 49,0000® available from Norton International. This adhesive layer can be coated on to the supporting substrate from a suitable solvent, such as tetrahydrofuran and/or dichloromethane solution, to enable a thickness thereof ranging, for example, from about 0.001 to abut 5 microns, and more specifically, from about 0.1 to about 3 microns.

The photoconductive imaging members can be economically prepared by a number of methods, such as the coating of the components from a dispersion, and more specifically, as illustrated herein. Thus, the photoresponsive imaging member disclosed herein can in embodiments be prepared by a number of known methods, the process parameters being dependent, for example, on the member desired. The photogenerating and charge transport components for the imaging members can be coated as solutions or dispersions onto a selected substrate by the use of a spray coater, dip coater, extrusion coater, roller coater, wire-bar coater, slot coater, doctor blade coater, gravure coater, and the like, and dried at from about 40° C. to about 200° C. for a suitable period of time, such as from about 10 minutes to about 10 hours under stationary conditions or in an air flow. The coating can be accomplished to provide a final coating thickness of from about 0.01 to about 30 microns after drying. The fabrication conditions for a given photoconductive layer can be tailored to achieve optimum performance and cost in the final members. The coating in embodiments can also be accomplished with spray, dip or wire-bar methods such that the final dry thickness of the photogenerating layer is, for example, from about 0.2 to about 30 microns, or about 0.2 to about 20 microns, or about 1 to about 5 microns, after being dried at, for example, about 40° C. to about 150° C. for about 5 to about 90 minutes.

Examples of substrate layers selected for the present imaging members can be opaque or substantially transparent, and can comprise any suitable material having the requisite mechanical properties. Thus, the substrate can comprise a layer of insulating material including inorganic or organic polymeric materials, such as MYLAR®, a commercially available polymer, MYLAR® containing titanium, a layer of an organic or inorganic material having a semiconductive surface layer, such as indium tin oxide, or aluminum arranged thereon, or a conductive material inclusive of aluminum, chromium, nickel, brass or the like. The substrate may be flexible, seamless, or rigid, and may have a number of many different configurations, such as, for example, a plate, a cylindrical drum, a scroll, an endless flexible belt, and the like. In one embodiment, the substrate is in the form of a seamless flexible belt. In some situations, it may be desirable to coat on the back of the substrate, particularly when the substrate is a flexible organic polymeric material, an anticurl layer, such as, for example, polycarbonate materials commercially available as MAKROLON®.

The thickness of the substrate layer depends on many factors, including economical considerations, thus this layer can be of substantial thickness, for example, over 3,000 microns, or of a minimum thickness. In one embodiment, the thickness of this layer is from about 75 microns to about 300 microns.

Generally, the thickness of the layer in contact with the supporting substrate depends on a number of factors, including the thickness of the substrate, and the amount of components contained in the single layer, and the like. Accordingly, the layer can be of a thickness of, for example, from about 3 microns to about 50 microns, and more specifically, from about 5 microns to about 30 microns. The maximum thickness of the layer in embodiments is dependent primarily upon factors, such as photosensitivity, electrical properties and mechanical considerations. The binder resin can be selected in various suitable amounts, for example, from about 5 to about 70, and more specifically, from about 10 to about 50 weight percent, and can comprise a number of known polymers such as poly(vinyl butyral), poly(vinyl carbazole), polyesters, polycarbonates, poly(vinyl chloride), polyacrylates and methacrylates, copolymers of vinyl chloride and vinyl acetate, phenoxy resins, polyurethanes, poly(vinyl alcohol), polyarylonitrile, polystyrene, and the like. In embodiments, single layer coating solvents selected can include, for example, ketones, alcohols, aromatic hydrocarbons, halogenated aliphatic hydrocarbons, ethers, amines, amides, esters, and the like. Specific examples include, but are not limited to, cyclohexanone, acetone, methyl ethyl ketone, methanol, ethanol, butanol, amyl alcohol, toluene, xylene, chlorobenzene, carbon tetrachloride, chloroform, methylene chloride, trichloromethylene, tetrahydrofuran, dioxane, diethyl ether, dimethyl formamide, dimethyl acetamide, butyl acetate, ethyl acetate, methoxyethyl acetate, and the like.

As optional adhesives usually in contact with the supporting substrate, there can be selected various known substances inclusive of polyesters as indicated herein, polyamides, poly(vinyl butyral), poly(vinyl alcohol), polyurethane and polyacrylonitrile. This layer is of a suitable thickness, for example a thickness of from about 0.001 micron to about 1 micron. Optionally, this layer may contain effective suitable amounts, for example from about 1 to about 10 weight percent, of conductive and nonconductive particles, such as zinc oxide, titanium dioxide, silicon nitride, carbon black, an the like, to provide, for example, in embodiments, further desirable electrical and optical properties.

Aryl amines selected for the hole transporting layer in contact with the photogenerating layer include molecules of the following formula

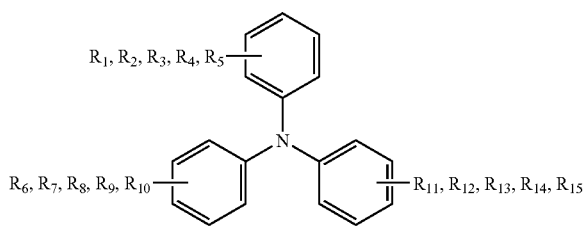

where $R_1$ through $R_{15}$ are independently chosen from the group alkyl, substituted alkyl, alkoxy, alkoxylalkyl, phenyl, naphthyl and higher aromatic compounds such as anthracene, other fused aromatic ring systems such as carbazole, stilbene and the like, halogen and hydrogen. Each of $R_1$ through $R_{15}$ can be selected to have a total atom count of between about 1 and about 50, between about 1 and about 10 or between about 1 and about 5. $R_1$ through $R_{15}$ can be selected in such a way that at least one of $R_1$ through $R_{15}$ is alkoxy, for example, methoxy, or alkyl, for example, methyl. A selected embodiment comprises bis(3,4-dimethylphenyl)-4-methoxphenyl amine) or tri-toylamine. Another selected embodiment comprises dimmers of the above but not of the benzidine type, for example 1,1-bis(di-4-tolylaminophenyl)cyclohexane. In yet another embodiment, example mixtures of arylamine compounds can be used for example mixtures of tri-tolylamine and 1,1-bis(di-4-tolylaminophenyl)cyclohexane.

Other known charge transport molecules can be selected, reference for example, U.S. Pat. Nos. 4,921,773 and 4,464,450, the disclosures of each of which are totally incorporated herein by reference.

Polymer binder examples for the hole transport molecules include components as illustrated, for example, in U.S. Pat. No. 3,121,006, the disclosure of which is totally incorporated herein by reference. Specific examples of polymer binder materials include polycarbonates, acrylate polymers, vinyl polymers, cellulose polymers, polyesters, polysiloxanes, polyamides, polyurethanes, and epoxies as well as block, random, or alternating copolymers thereof. Specifically, electrically inactive binders can be selected comprised of polycarbonate resins with a molecular weight of from about 20,000 to about 100,000 or more specifically with a molecular weight of from about 50,000 to about 100,000.

Further included are methods of imaging and printing with the photoresponsive or photoconductive members illustrated herein. These methods generally involve the formation of an electrostatic latent image on the imaging member, followed by developing the image with a toner composition comprised, for example, of thermoplastic resin, colorant, such as pigment, charge additive, and surface additives, reference for example U.S. Pat. Nos. 4,560,635; 4,298,697; and 4,338,380, the disclosures of each of which are totally incorporated herein by reference, subsequently transferring the image to a suitable substrate, and permanently affixing, for example, with heat, the image thereto. In those environments wherein the member is to be used in a printing mode, the imaging method is similar with the exception that the exposure step can be accomplished with a laser device or image bar.

EXAMPLES

The following Examples are being submitted to further define various species of the present disclosure. These Examples are intended to be illustrative only and are not intended to limit the scope of the present disclosure. Also, parts and percentages are by weight unless otherwise indicated.

Example I 3,4,5,6-tetrachlorophthalic anhydride (3.13 grams, 0.011 moles), 2,3,-diaminonaphthalene (1.58 grams, 0.011 moles), and N-methyl-2-pyrrolidone (NMP) (30 milliliters) were heated to reflux for 2 hours, cooled to room temperature, and filtered. The filter cake was washed with N,N-dimethylformamide (4 washes of 25 milliliters each wash) and methanol (4washes of 25 milliliters each wash) and dried at about 80° C. under vacuum of about 10 millimeters mercury overnight to yield 2.8 grams of tetrachlorobenzamidazolebenzene having the structure (3). The 2.8 grams of tetrachlorobenzamidazolebenzene compound was purified by train sublimation as known to those skilled in the art (for example as described in H. J. Wagner, R. O. Loutfy and C.-K. Hsaio, *J. Mater. Sc.* 17, 2781, 1982) to yield 2.6 grams of tetrahalobenzamidazolebenzene compound whose purity and absolute identify was comfirmed using primarily $^1$H nuclear magnetic resonance spectroscopy using $CDCl_3$/TFA-d 3/1 v/v (a mixture of deuterated chloroform ($CDCL_3$) and deuterated trifluroacetic acid (TFA-d) mixed in a ratio of 3 parts to 1 part, respectively, by volume) as the solvent and tetramethylsilane (TMS) as an internal standard) and elemental analysis.

Example II 3,4,5,6-tetrachlorophthalic anhydride (6.0 grams, 0.21 moles), 3,3'-diaminobenzidine (2.14 grams, 0.010 moles), and 0.6 grams zinc (II) acetate dehydrate were placed in a vessel containing 125 milliliters of N-methyl-2-pyrrolidone, heated to reflux for 2 hours, cooled to room temperature and filtered. The cake was washed three times with 25 milliliters each time of N,N-dimethylformamide, washed three times with 25 milliliters each time of methanol, and dried under vacuum overnight to yield 7.14 grams of bis(tetrachlorophenyl)biphenylbisimidazole compound. 2.4 grams of compound was purified by train sublimation (for example as described in H. J. Wagner, R. O. Loutfy and C.-K. Hsaio, *J. Mater. Sc.* 17, 2781, 1982) to yield 1.66 grams of pure compound whose purity and absolute identify was comfirmed using primarily $^1$H nuclear magnetic resonance spectroscopy (using (using $CDCl_3$/TFA-d 3/1 v/v as the solvent and TMS as the internal standard) and elemental analysis.

Example III 3,4,5,6-tetrachlorophthalic anhydride (3.13 grams, 0.011 moles), o-phenylenediamine (1,2-diaminobenzene, 1.19 grams, 0.011 moles), and N-methyl-2-pyrrolidone (NMP) (30 milliliters) were heated to reflux for 2 hours, cooled to room temperature, and filtered. The filter cake was washed with N,N-dimethylformamide (4 washes of 25 milliliters each wash) and methanol (4 washes of 25 milliliters each wash) and dried (at 80° C.) under vacuum (10mmHg) overnight to yield 2.8 grams of tetrachlorobenzamidazolebenzene having the structure (3). The 2.8 grams of tetrachlorobenzamidazolebenzene compound was purified by train sublimation (for example as described in H. J. Wagner, R. O. Loutfy and C.-K. Hsaio, *J. Mater. Sc.* 17, 2781, 1982.) to yield 2.6 grams of tetrahalobenzamidazolebenzene compound whose purity and absolute identify was confirmed using primarily $^1$H nuclear magnetic resonance spectroscopy (using $CDCl_3$/TFA-d 3/1 v/v as the solvent and TMS as an internal standard) and elemental analysis.

Example IV

Preparation of Evaporated Pigment Generator Layer

Thin film of 5000 Å was prepared by vacuum evaporation in a Balzer BAE080™ coater. Compounds as described in Examples I-III were loaded into a tantalum boat, and then capped after filling. The system pressure remained stable at <$10^{-5}$ mmHg during the evaporation. The boat was gradually heated until it reached the temperature where the pigment began to sublime. The pigment vapor deposited onto a titanized MYLAR® substrate of 75 microns in thickness which substrate contained thereon a silane layer, 0.1 micron in thickness, situated above the source at a control rate of 2-4 Å/s, as monitored by a Quartz crystal monitor.

Example V

Preparation of Binder Generator Layer 0.2 gram of compounds as described in Examples I-III were mixed with 0.05 gram of poly-N-vinylcarbazole (PVK) and 10.5 grams dichloromethane in a 30 milliliter glass bottle containing 70 grams ⅛"stainless steel shots, then placed on a roll mill for 3 days with gentle to moderate rolling. Using a film applicator with a gap of 1.5 mil, the pigment dispersion was coated on a titanized MYLAR® substrate of 75 microns in thickness which substrate contained thereon a silane layer, 0.1 micron in thickness. Thereafter, the photogenerator layer formed was dried in a forced air oven at 135° C. for 20 minutes.

Example VI

Preparation of Hole Transport Layer

A transport layer solution was prepared by mixing 2.025 grams of polycarbonate (PC(Z)400), 0.675 grams of tritoylamine, 0.675 grams of 1,1-bis-(N,N-ditoyl4-aminophenyl)cyclohexane and 15.38 grams of methylene chloride. The resulting solution was coated onto the above photogenerating layer using a film applicator of 10 mil gap. The resulting photoconductive member was then dried at 135° C. in a forced air oven for 20 minutes. The final dried thickness of the transport layer was 25 microns.

Example VII

Electrical Measurements of Device

The xerographic electrical properties of the above-prepared photoconductive imaging members and other similar members can be determined by known means, including electrostatically charging the surfaces thereof with a corona discharge source until the surface potentials, as measured by a capacitively coupled probe attached to an electrometer, attained an initial value Vo of about −800 volts. After resting for 0.5 second in the dark, the charged members attained a surface potential of $V_{ddp}$, dark development potential. Each member was then exposed to light from a filtered Xenon lamp thereby inducing a photodischarge which resulted in a reduction of surface potential to a $V_{bg}$ value, background potential. The percent of photodischarge was calculated as $100 \times (V_{ddp} - V_{bg})/V_{ddp}$. The desired wavelength and energy of the exposed light was determined by the type of filters placed in front of the lamp. The monochromatic light photosensitivity was determined using a narrow band-pass filter. The photosensitivity of the imaging member was usually provided in terms of the amount of exposure in ergs/cm², designated as $E_{1/2}$, required to achieve 50 percent photodischarge from $V_{ddp}$ to half of its initial value. The higher the photosensitivity, the smaller is the $E_{1/2}$ value. The device was finally exposed to an erase lamp of appropriate light intensity and any residual potential ($V_{residual}$) was measured. The imaging members were tested with an exposure monochromatic light at a wavelength of 400 nanometers and an erase broad-band light with the wavelength of about 400 to about 800 nanometers.

TABLE 1

| Pigment | DD (500 ms) (−V) | S (V.erg/cm²) | $E_{1/2}$ (ergs/cm²) | $E_{7/8}$ (ergs/cm²) | Vr (−V) |
|---|---|---|---|---|---|
| Example I | 1 | 76 | 5.14 | 11.33 | 6 |
| Example II | 4 | 35 | n/a | n/a | 24 |
| Example III | 13 | 16 | n/a | n/a | 303 |

DD—dark decay
S—sensitivity
$E_{1/2}$—exposure to decrease charge to ½ initial value
$E_{7/8}$—exposure to decrease charge to ⅞ initial value A photoconductive imaging member fabricated by the process of Example IV using the pigment of Example I had a dark decay of 1 volts/second, a sensitivity of 76 V.erg/cm², an $E_{1/2}$ of 5.14 ergs/cm² and the $V_{residual}$ was 6 volts for negative charging. The member was sensitive to blue light of a wavelength of 400 nanometers, and which wavelength was generated from a 400 nanometer single-band pass filter placed in front of a xenon lamp.

A photoconductive imaging member fabricated by the process of Example IV using the pigment of Example II had a dark decay of 4 volts/second, a sensitivity of 35 V.erg/cm² and the $V_{residual}$ was 24 volts for negative charging. The member was sensitive to blue light of a wavelength of 400 nanometers, and which wavelength was generated from a 400 nanometer single-band pass filter placed in front of a xenon lamp.

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A compound having the following formula

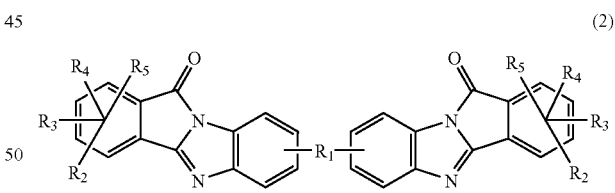

(2)

wherein $R_1$ is selected from the group consisting of a bond, alkyl, aryl, hydrocarbon, chlorine, bromine, and iodine, and wherein each of $R_2$, $R_3$, $R_4$, $R_5$, is halogen.

2. The compound of claim 1, wherein the alkyl is 1 to 25 carbon atoms.

3. The compound of claim 1, wherein the hydrocarbon is arranged to form a ring system or a multi-ring system.

4. The compound of claim 1, wherein the aryl is 6 to 48 carbon atoms.

5. The compound of claim 1, wherein $R_1$ is selected from the group consisting of alkyl, aryl, hydrocarbon, chlorine, bromine, and iodine, and wherein $R_2$, $R_3$, $R_4$, $R_5$, are the same or different and are independently selected from the group consisting of fluorine, chlorine, bromine, and iodine.

6. A compound having the following formula

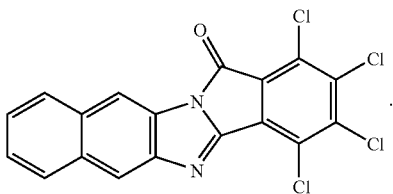

7. A compound having the following formula

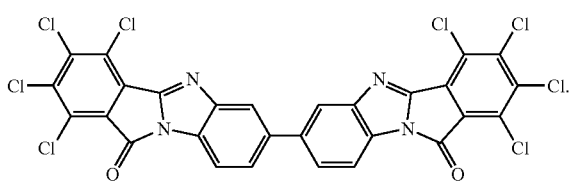

8. A bis(tetrahalophenyl)biphenylbisimidazole compound of the following formula

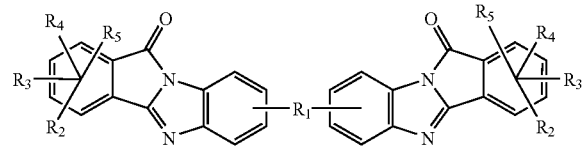

(2)

wherein $R_1$ is selected from the group consisting of a bond, alkyl, aryl, hydrocarbon, chlorine, bromine, and iodine, and wherein each of $R_2$, $R_3$, $R_4$, and $R_5$, are halogen.

9. The compound of claim 8, wherein the alkyl is 1 to 25 carbon atoms.

10. The compound of claim 8, wherein the hydrocarbon is arranged to form a ring system or a multi-ring system.

11. The compound of claim 8, wherein the aryl is 6 to 48 carbon atoms.

12. The compound of claim 8, wherein halogen is selected from the group consisting of fluorine, chlorine, bromine, and iodine.

13. The compound of claim 8, wherein alkyl is selected from the group consisting of methyl, ethyl, propyl, butyl, pentyl, and higher carbon number straight chained alkyl groups.

14. The compound of claim 8, wherein aryl is selected from the group consisting of phenyl, naphthyl, anthranyl and higher fused aromatic ring systems.

15. A compound having the following formula

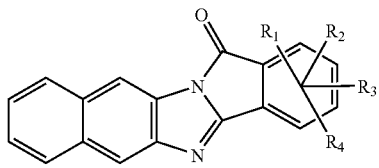

wherein each of $R_1$, $R_2$, $R_3$, $R_4$ is a halogen.

16. A compound having the following formula

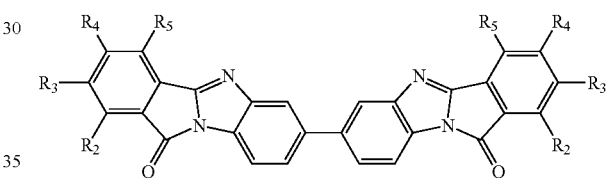

wherein each of $R_2$, $R_3$, $R_4$, and $R_5$ is a halogen.

* * * * *